(12) United States Patent
Stopek

(10) Patent No.: US 9,012,467 B2
(45) Date of Patent: Apr. 21, 2015

(54) COMPOSITIONS FOR INTRATUMORAL ADMINISTRATION

(75) Inventor: Joshua Stopek, Guilford, CT (US)

(73) Assignee: Covidien LP, Mansfield, MA (US)

( * ) Notice: Subject to any disclaimer, the term of this patent is extended or adjusted under 35 U.S.C. 154(b) by 478 days.

(21) Appl. No.: 12/905,596

(22) Filed: Oct. 15, 2010

(65) Prior Publication Data

US 2011/0112123 A1     May 12, 2011

Related U.S. Application Data

(60) Provisional application No. 61/259,846, filed on Nov. 10, 2009.

(51) Int. Cl.
| | |
|---|---|
| *A61K 31/513* | (2006.01) |
| *A61K 31/11* | (2006.01) |
| *A61K 9/00* | (2006.01) |
| *A61K 31/115* | (2006.01) |
| *A61K 31/353* | (2006.01) |
| *A61K 45/06* | (2006.01) |
| *A61K 47/22* | (2006.01) |
| *A61P 35/00* | (2006.01) |

(52) U.S. Cl.
CPC ............. *A61K 31/11* (2013.01); *A61K 9/0019* (2013.01); *A61K 31/115* (2013.01); *A61K 31/353* (2013.01); *A61K 45/06* (2013.01); *A61K 47/22* (2013.01)

(58) Field of Classification Search
CPC ..................................................... A61K 31/513
USPC ................................................ 514/183, 274
See application file for complete search history.

(56) References Cited

U.S. PATENT DOCUMENTS

| | | | |
|---|---|---|---|
| 5,459,160 A | 10/1995 | Fujii et al. | |
| 6,624,138 B1 | 9/2003 | Sung et al. | |
| 7,101,857 B2 | 9/2006 | Sung et al. | |
| 2005/0208122 A1 | 9/2005 | Allen et al. | |
| 2007/0020225 A1 | 1/2007 | Abramson et al. | |
| 2009/0123581 A1 | 5/2009 | Bedran-Russo | |

FOREIGN PATENT DOCUMENTS

WO    WO 2009/105265 A2    8/2009

OTHER PUBLICATIONS

Hsing-Wen Sung et al., Stability of a biological tissue fixed with a naturally occurring crosslinking agent (genipin), accepted Nov. 22, 2000 (2001), John Wiley & Sons, Inc., 55, p. 539 col. 1 Fixation Process.*
Changyou Gao et al.,Nanomedicine: Nanotechnology, Biology, and Medicine, Hollow chitosan-alginate mutli-layer microcapsules as drug delivery vehicle: doxorubicin loading and in vitro and in vivo studies, accepted Nov. 21, 2006 (2007) p. 72 col. 1.*
Ning Wang, Meifen Zhu, Sai-Wah Tsao, Kwan Man, Zhangjin Zhang, Yibin Feng, Up-Regulation of TIMP-1 by Genipin Inhibits MMP-2 Activities and Suppresses the Metastatic Potential of Human Hepatocellular Carcinoma, PLOS ONE, Sep. 2012, vol. 7, Issue 9, e46318, 1-11.*
Sarah Williams, Daniel Palmer and Philip Johnson, New medical options for liver tumours, Clin Med, 2007;7:351-6.*
Eugene P. Goldberg, Ahmad R. Hadba, Brett A. Almond and James S. Marotta, Intratumoral cancer chemotherapy and immunotherapy: opportunities for nonsystemic preoperative drug delivery, Journal of Pharmacy and Pharmacology, 2002, 54: 159-180.*
European Search Report for EP 10251911.3-2112 date of completion is Mar. 11, 2011 (3 pages).
Huang K S et al.: "Microfluidic Controlling Monodisperse Microdroplet for 5-Fluorouracil Loaded Genipin-Gelatin Microcapsules", Journal of Controlled Release, Elsevier, Amsterdam, NL, vol. 137, No. 1, Jul. 1, 2009 pp. 15-19 (XP026161192).
Ohya Y et al.: "Preparation of Albumin Microspheres Grafted Galactose Residues Through Polyethylene-Glycol Spacers, Release Behavior of 5-Fluorouracil From Them, and Their Lectin-Mediated Aggregation", Journal of Macromolecular science: Part A—Chemistry, Marcel Dekker, NY, NY, vol. A28, No. 8, Jan. 1, 1991, pp. 743-760 (XP002060122).

* cited by examiner

*Primary Examiner* — Kendra D Carter
*Assistant Examiner* — Jason A Deck

(57) ABSTRACT

The present disclosure describes compositions for intratumoral administration which include a tissue-stabilizing agent and a therapeutic agent.

8 Claims, 1 Drawing Sheet

COMPOSITIONS FOR INTRATUMORAL ADMINISTRATION

CROSS-REFERENCE TO RELATED APPLICATION

The present application claims the benefit of and priority to U.S. Provisional Application Ser. No. 61/259,846, filed on Nov. 10, 2009, the entire disclosure of which is incorporated herein by reference.

BACKGROUND

1. Technical Field

The present disclosure relates to compositions for intratumoral administration which include a tissue-stabilizing agent and a therapeutic agent in a pharmaceutically acceptable carrier.

2. Background of Related Art

The treatment of many cellular disorders, for example, tumors, and other hyperproliferative diseases, may involve the systemic use of therapeutic agents. These agents may exert their activity in a variety of ways. In many, if not most instances, the therapeutic agent may not address the abnormal cell specifically, but rather tends to exert its effectiveness systemically across all cells. Systemic administration may therefore expose both abnormal cells and healthy, normal cells to the effects of the therapeutic agent. Although potentially effective therapeutically against the abnormal cells, systemic administration of the therapeutic effect may be detrimental or cause detrimental side effects to the normal healthy cells. This may result in a smaller amount of the intended dosage of the therapeutic agent reaching and addressing the abnormal cells or tumor. In addition, a greater amount of the intended dosage of the therapeutic agent may reach and address the normal healthy cells. Systemic delivery of therapeutic agents may hinder the dosing parameters from being maximized because of the potentially harmful side effects.

For example, anti-neoplastic agents may be cytotoxic. The anti-neoplastic agents may exert their cytotoxic activity in a variety of ways, sometimes interfering with a cellular function essential for the replication and/or viability of the cell. Many anti-neoplastic agents may be administered systemically and may not be designed specifically to attack the abnormal cells only, but rather may be designed to exert their effectiveness due to the more rapid proliferation of the abnormal cell, as compared to normal healthy cells. While many organs of the body of a mammalian host regenerate cells rather slowly, there may also be other organs, particularly bone marrow, which involve rapid proliferation of stem cells. Therefore, anti-neoplastic agents may not only affect the slowly regenerating cells detrimentally, but may also have a particularly pernicious effect on bone marrow production and the immune system.

Despite the possible disadvantages and side effects of employing the systemic use of therapeutic agents, this method has found extensive application because the agents may have provided some positive results. However, there remains a substantial interest in being able to employ therapeutic agents in a manner which is less systemic, i.e., directed more specifically toward the abnormal cells, while simultaneously protecting sensitive normal cells, both in the vicinity of and distant from the site of the abnormal cells.

SUMMARY

Accordingly, the present disclosure describes compositions suitable for intratumoral administration which include a combination of at least one tissue-stabilizing agent and at least one therapeutic agent in a pharmaceutically acceptable carrier. Upon administration, the tissue-stabilizing agent begins to cross-link with the tumoral tissue thereby substantially inhibiting the migration of the therapeutic agent from the site of administration. By controlling the migration of the therapeutic agent from inside the tumor, the primary therapeutic effect of the therapeutic agent may be prolonged and enhanced against the tumoral tissue. In addition, tissue stabilization via cross-linking may improve tumor stiffness, making resection of the tumor easier, and further slow tumor proliferation and/or metastasis. In some embodiments, the tissue-stabilizing agent may also display a color change following interaction with the tumoral tissue thereby providing visual identification of the tumor site.

Methods of intratumoral therapy are also described.

BRIEF DESCRIPTION OF THE DRAWINGS

The accompanying drawings, which are incorporated in and constitute a part of the present disclosure, illustrate embodiments of the disclosure and, together with a general description given herein, and the detailed description of the embodiments provided herein, serve to explain the principles of the present disclosure.

DETAILED DESCRIPTION

Figure 1A:
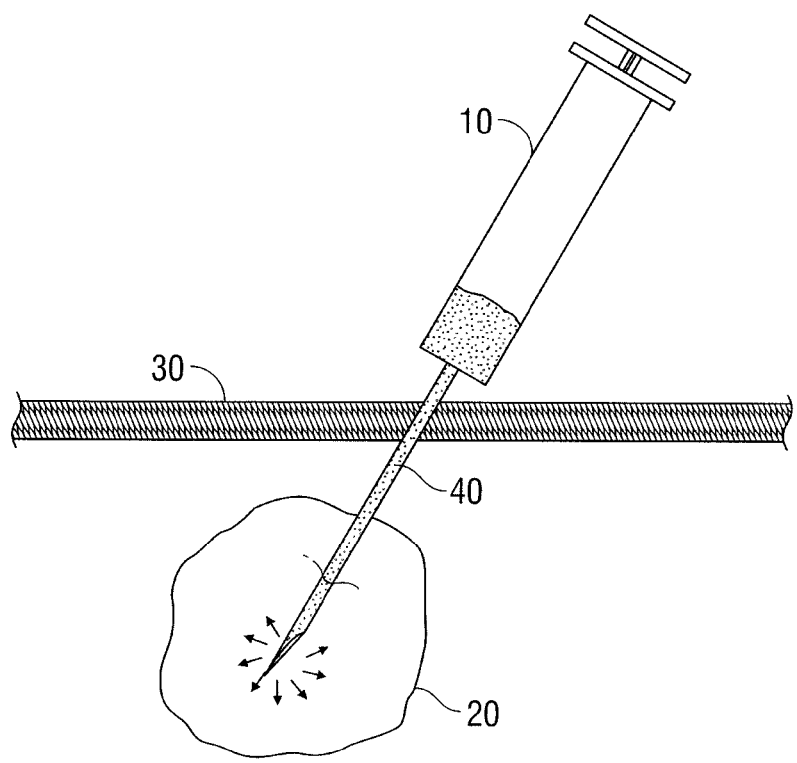
FIGS. 1A and 1B schematically illustrate intratumoral administration of a composition containing a tissue-stabilizing agent and a therapeutic agent in a pharmaceutically acceptable carrier.

Compositions and methods are provided for the treatment of hyperproliferative diseases including, but not limited to cancers, abnormal cellular growths, psoriasis, and the like. Hyperproliferative growth may include neoplastic or preneoplastic lesions or conditions such as psoriasis, keloids, nodules, or warts. It will be understood that the terms neoplastic and preneoplastic lesions may refer to any new or abnormal growth, such as, for example: cancer, oncogenically transformed cells, carcinomas, melanomas, lymphomas, neuromas, spiromas, fibromas, blastomas, chodromas, gliomas, myxomas, thecomas, myelomas, both benign and malignant tumors, and sarcomas. Some non-limiting examples of cancers which may be treated with the compositions include brain cancer, bone cancer, bladder cancer, breast cancer, pancreatic cancer, testicular cancer, spinal cancer, skin cancer, prostate cancer, colon cancer, lung cancer, thyroid cancer, and the like.

The treatment may be employed by administering the compositions described herein directly into a tumor, i.e., intratumorally. The term intratumorally is intended to include administration into a lesion, i.e., intralesionally.

The therapeutic compositions may include at least one therapeutic agent and at least one tissue-stabilizing agent. The compositions may be administered to the region of the tumor either intratumorally by injection or by being implanted into at least a portion of the tumor.

The term "tissue-stabilizing agent" refers to any agent which interacts with the tumoral tissue to cross-link and/or fix the tumoral tissue. The terms "cross-link" and "fix" are used interchangeably to represent a chemical interaction between the stabilizing agent and the tumoral tissue to create a hardened or stiffened mass of tumoral tissue. By employing the compositions described herein, the therapeutic agent may be initially localized within the confines of the tumor while the tissue-stabilizing agent cross-links the tumor tissue. The hardened, cross-linked tumor may reduce the escape of the therapeutic agent thereby enhancing the local effect of the therapeutic agent contained inside the tumor while the blood-levels of the therapeutic agent outside the perimeter of the tumor remain low. After the tumor has been cross-linked, the tumor may also act as a controlled release reservoir, providing drainage to the lymph for the therapeutic agent which may slowly release the therapeutic agent over time. In this way, an enhanced therapeutic gain may be achieved. The therapeutic effect on the stabilized tumoral cells may be greater, additionally susceptible normal cells remote from the administration site may be less affected.

Some non-limiting examples of suitable tissue-stabilizing agents may include formaldehyde, glutaraldehyde, dialdehyde starch, glycoaldehyde, cyanamide, diimides, diisocyanates, succinimidyl esters, iridoid compounds and combinations thereof.

In some embodiments, the therapeutic agent may be combined with an iridoid compound as the tissue-stabilizing agent. Any iridoid compound having the ability to cross-link tissue may be used as the tissue stabilizing agent in the present processes. Illustrative examples include the aglycones of geniposide, gardenoside, geniposidic acid, and the like. These iridoid compounds may be prepared in accordance with the disclosures in Japanese Patent Publication No. 57-14781 and Japanese Patent Public Disclosure No. 61-47167. In embodiments, genipin may be used as the tissue stabilizing agent.

The term "genipin" refers to the naturally occurring compound iridoid glycoside present in fruits (Gardenia jasmindides Ellis) and to its stereoisomers and mixtures thereof. Genipin, an aglycone of geniposide, may be prepared from geniposide by oxidation followed by reduction and hydrolysis or by enzymatic hydrolysis. Alternatively, racemic genipin may be prepared synthetically. Any natural or synthetic version of genipin may be used as a tissue-stabilizing agent in the compositions described herein.

Genipin has a low acute toxicity, with $LD_{50}$ i.v. 382 mg/k in mice. It may therefore be less toxic than glutaraldehyde and many of the other tissue-stabilizing agents. As described below, genipin is shown to be an effective crosslinking agent for treatment of abnormal cellular growth and may be suitable for intratumoral administration.

Genipin may react with the free amino groups found in tumoral tissues. In some instances, the interaction between the genipin and the tumoral tissue may lead to the production of a blue pigment which may more clearly define geometry and the topography of the tumoral tissue (easily identifiable to the surgeon). The blue-pigment may be produced as a result of the oxygen radical-induced polymerization and dehydrogenation of several intermediary pigments.

In other embodiments, the composition described herein may include glutaraldehyde as the tissue-stabilizing agent. By means of its aldehyde functional groups, glutaraldehyde reacts primarily with the amine groups of the tumoral tissue. In polymerization, the aldehyde functional groups of 2 glutaraldehyde molecules may undergo an aldol condensation. With glutaraldehyde polymerization, subsequent to stabilization, a network crosslinking structure may be created intramolecularly and/or intermolecularly within the tumoral tissue.

The tissue-stabilizing agents may be used in amounts that are effective in cross-linking or fixing the tumoral tissue, which may vary widely depending largely on the particular stabilizing agent being used. The amount of stabilizing agent incorporated into the composition may also depend upon the size of the tumor or abnormal growth, and the length of time required for the stabilizing agent to fix the tumoral tissue.

One critical upper limit on the amount of tissue-stabilizing agent incorporated into the composition may be defined by the toxicity or cytotoxicity of the agent. The tissue-stabilizing agent should not be administered in amounts or concentrations which are known to be toxic or cytotoxic to the surrounding tissue or body. Another factor which may determine an upper limit on the amount of tissue-stabilizing agent incorporated into the compositions described herein includes the physical characteristics desired for the composition, such as the viscosity of a suitable solution or dispersion. The lower limit of the tissue-stabilizing agent incorporated into the delivery system is dependent upon the ability of the agent to cross-link the tumoral tissue and/or the length of time needed to stabilize the tumoral tissue. Thus, the amount of the tissue-stabilizing agent should not be so small that it fails to produce fixation of the tumoral tissue, nor so large that the tissue-stabilizing agent cross-links with the surrounding healthy tissue in an uncontrollable manner.

Typically, within these limits, amounts of the tissue-stabilizing agents may represent from about 0.1% to about 90% by weight of the composition. In some embodiments, the tissue-stabilizing agent may represent from about 1% to about 70% by weight of the composition. However, lesser amounts may also be used.

The term "therapeutic agent", as used herein, is used in its broadest sense and includes any substance or mixture of substances that provide clinical use. A therapeutic agent could be any agent that provides a therapeutic or prophylactic effect, a compound that affects or participates in tissue growth, cell growth, cell differentiation, a compound that may be able to invoke a biological action such as an immune response, or could play any other role in one or more biological processes.

The therapeutic agent may be incorporated into the composition in any physical form suitable for intratumoral delivery. Some non-limiting examples include powders, particles, fibers, beads, microspheres, solutions, suspensions, and the like.

Examples of therapeutic agents which may be utilized in accordance with the present disclosure include drugs, amino acids, peptides, polypeptides, proteins, polysaccharides, muteins, immunoglobulins, antibodies, cytokines (e.g., lymphokines, monokines, chemokines), blood clotting factors, hemopoietic factors, interleukins (1 through 18), interferons (e.g., β-IFN, α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, fibrin, thrombin, fibrinogen, synthetic thrombin, synthetic fibrin, synthetic fibrinogen, gonadotropins (e.g., FSH, LH, CG, etc.), hormones and hormone analogs (e.g., growth hormone, luteinizing hormone releasing factor), vaccines (e.g., tumoral, bacterial and viral antigens); somatostatin; antigens; blood coagulation factors; growth factors (e.g., nerve growth factor, insulin-like growth factor); bone morphogenic proteins, TGF-B, protein inhibitors, protein antagonists, and protein agonists; nucleic acids, such as antisense molecules, DNA, RNA, RNAi; oligonucleotides; polynucleotides; cells, viruses, anti-tumoral antibodies, antigens and antigen fragments, tumor cell and tumor cell fragments (fragments of tumor which may invoke an immune response to the tumor) and ribozymes.

In embodiments, the therapeutic agent may include at least one drug. The term "drug" is intended to include any substance that, when introduced or absorbed into the body of a living organism, alters normal bodily or cellular function.

Some non-limiting examples of suitable drugs, including combinations and alternative forms of the drugs such as alternative salt forms, free acid form, free base forms, pro-drugs and hydrates, include: analgesics/antipyretics (e.g., aspirin, acetaminophen, ibuprofen, naproxen sodium, buprenorphine, propoxyphene hydrochloride, propoxyphene napsylate, meperidine hydrochloride, hydromorphone hydrochloride, morphine, oxycodone, codeine, dihydrocodeine bitartrate, pentazocine, hydrocodone bitartrate, levorphanol, diflunisal, trolamine salicylate, nalbuphine hydrochloride, mefenamic acid, butorphanol, choline salicylate, butalbital, phenyltoloxamine citrate, diphenhydramine citrate, methotrimeprazine, cinnamedrine hydrochloride, and meprobamate); antiasthmatics (e.g., ketotifen and traxanox); antibiotics (e.g., neomycin, streptomycin, chloramphenicol, cephalosporin, ampicillin, penicillin, tetracycline, and ciprofloxacin); antidepressants (e.g., nefopam, oxypertine, doxepin, amoxapine, trazodone, amitriptyline, maprotiline, phenelzine, desipramine, nortriptyline, tranylcypromine, fluoxetine, imipramine, imipramine pamoate, isocarboxazid, trimipramine, and protriptyline); antidiabetics (e.g., biguanides and sulfonylurea derivatives); antifungal agents (e.g., griseofulvin, ketoconazole, itraconazole, amphotericin B, nystatin, and candicidin); antihypertensive agents (e.g., propanolol, propafenone, oxyprenolol, nifedipine, reserpine, trimethaphan, phenoxybenzamine, pargyline hydrochloride, deserpidine, diazoxide, guanethidine monosulfate, minoxidil, rescinnamine, sodium nitroprusside, rauwolfia serpentine, alseroxylon, and phentolamine); anti-inflammatories (e.g., (non-steroidal) indomethacin, ketoprofen, flurbiprofen, naproxen, ibuprofen, ramifenazone, piroxicam, (steroidal) cortisone, dexamethasone, fluazacort, deflazacort, celecoxib, rofecoxib, hydrocortisone, prednisolone, and prednisone); antineoplastics (e.g., cyclophosphamide, actinomycin, bleomycin, dactinomycin, daunorubicin, doxorubicin, epirubicin, mitomycin, methotrexate, fluorouracil, gemcitabine, carboplatin, carmustine (BCNU), methyl-CCNU, cisplatin, etoposide, camptothecin and derivatives thereof, phenesterine, paclitaxel and derivatives thereof, docetaxel and derivatives thereof, vinblastine, vincristine, goserelin, leuprolide, tamoxifen, interferon alfa, retinoic acid (ATRA), nitrogen mustard alkylating agents, and piposulfan); antianxiety agents (e.g., lorazepam, buspirone, prazepam, chlordiazepoxide, oxazepam, clorazepate dipotassium, diazepam, hydroxyzine pamoate, hydroxyzine hydrochloride, alprazolam, droperidol, halazepam, chlormezanone, and dantrolene); immunosuppressive agents (e.g., cyclosporine, azathioprine, mizoribine, and FK506 (tacrolimus)); antimigraine agents (e.g., ergotamine, propanolol, isometheptene mucate, and dichloralphenazone); sedatives/hypnotics (e.g., barbiturates such as pentobarbital, pentobarbital, and secobarbital; and benzodiazapines such as flurazepam hydrochloride, triazolam, and midazolam); antianginal agents (e.g., beta-adrenergic blockers; calcium channel blockers such as nifedipine, and diltiazem; and nitrates such as nitroglycerin, isosorbide dinitrate, pentearythritol tetranitrate, and erythrityl tetranitrate); antipsychotic agents (e.g., haloperidol, loxapine succinate, loxapine hydrochloride, thioridazine, thioridazine hydrochloride, thiothixene, fluphenazine, fluphenazine decanoate, fluphenazine enanthate, trifluoperazine, chlorpromazine, perphenazine, lithium citrate, and prochlorperazine); antimanic agents (e.g., lithium carbonate); antiarrhythmics (e.g., bretylium tosylate, esmolol, verapamil, amiodarone, encamide, digoxin, digitoxin, mexiletine, disopyramide phosphate, procainamide, quinidine sulfate, quinidine gluconate, quinidine polygalacturonate, flecamide acetate, tocamide, and lidocaine); antiarthritic agents (e.g., phenylbutazone, sulindac, penicillanine, salsalate, piroxicam, azathioprine, indomethacin, meclofenamate, gold sodium thiomalate, ketoprofen, auranofin, aurothioglucose, and tolmetin sodium); antigout agents (e.g., colchicine, and allopurinol); anticoagulants (e.g., heparin, heparin sodium, and warfarin sodium); thrombolytic agents (e.g., urokinase, streptokinase, and alteplase); antifibrinolytic agents (e.g., aminocaproic acid); hemorheologic agents (e.g., pentoxifylline); antiplatelet agents (e.g., aspirin); anticonvulsants (e.g., valproic acid, divalproex sodium, phenyloin, phenyloin sodium, clonazepam, primidone, phenobarbital, carbamazepine, amobarbital sodium, methsuximide, metharbital, mephobarbital, mephenyloin, phensuximide, paramethadione, ethotoin, phenacemide, secobarbital sodium, clorazepate dipotassium, and trimethadione); antiparkinson agents (e.g., ethosuximide); antihistamines/antipruritics (e.g., hydroxyzine, diphenhydramine, chlorpheniramine, brompheniramine maleate, cyproheptadine hydrochloride, terfenadine, clemastine fumarate, triprolidine, carbinoxamine, diphenylpyraline, phenindamine, azatadine, tripelennamine, dexchlorpheniramine maleate, methdilazine, and); agents useful for calcium regulation (e.g., calcitonin, and parathyroid hormone); antibacterial agents (e.g., amikacin sulfate, aztreonam, chloramphenicol, chloramphenicol palmitate, ciprofloxacin, clindamycin, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, and colistin sulfate); antiviral agents (e.g., interferon alpha, beta or gamma, zidovudine, amantadine hydrochloride, ribavirin, and acyclovir); antimicrobials (e.g., cephalosporins such as cefazolin sodium, cephradine, cefaclor, cephapirin sodium, ceftizoxime sodium, cefoperazone sodium, cefotetan disodium, cefuroxime axetil, cefotaxime sodium, cefadroxil monohydrate, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, and cefuroxime sodium; penicillins such as ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G procaine, methicillin sodium, and nafcillin sodium; macrolides such as, azithromycin, clarithromycin, and erythromycins such as erythromycin ethylsuccinate, erythromycin, erythromycin estolate, erythromycin lactobionate, erythromycin stearate, and erythromycin ethylsuccinate; and tetracyclines such as tetracycline hydrochloride, doxycycline hyclate, and minocycline hydrochloride); anti-infectives (e.g., GM-CSF); bronchodilators (e.g., sympathomimetics such as epinephrine hydrochloride, metaproterenol sulfate, terbutaline sulfate, isoetharine, isoetharine mesylate, isoetharine hydrochloride, albuterol sulfate, albuterol, bitolterolmesylate, isoproterenol hydrochloride, terbutaline sulfate, epinephrine bitartrate, metaproterenol sulfate, epinephrine, and epinephrine bitartrate; anticholinergic agents such as ipratropium bromide; xanthines such as aminophylline, dyphylline, metaproterenol sulfate, and theophylline; mast cell stabilizers such as cromolyn sodium; inhalant corticosteroids such as beclomethasone dipropionate (BDP), and beclomethasone dipropionate monohydrate; salbutamol; ipratropium bromide; budesonide; salmeterol; xinafoate; triamcinolone; nedocromil sodium; flunisolide; fluticasone propionate; steroidal compounds and hormones (e.g., androgens such as danazol, testosterone cypionate, fluoxymesterone, ethyltestosterone, testosterone enathate, methyltestosterone; estrogens such as estradiol, estropipate, and conjugated estrogens; progestins such as methoxyprogesterone acetate, and norethindrone acetate; corticosteroids such as triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate, methylprednisolone sodium succinate, hydrocortisone sodium succinate, triamcinolone hexacetonide, hydrocortisone, hydrocortisone cypionate, prednisolone, fludrocortisone acetate, paramethasone acetate, prednisolone tebutate, prednisolone acetate, prednisolone sodium phosphate, and thyroid hormones such as levothyroxine sodium); hypoglycemic agents (e.g., human insulin, purified beef insulin, purified pork insulin, glyburide, metformin, chlorpropamide, glipizide, tolbutamide, and tolazamide); hypolipidemic agents (e.g., clofibrate, dextrothyroxine sodium, probucol, pravastitin, atorvastatin, lovastatin, and niacin); proteins (e.g., DNase, alginase, superoxide dismutase, and lipase); nucleic acids (e.g., sense or anti-sense nucleic acids encoding any therapeutically useful protein, including any of the proteins described herein); agents useful for erythropoiesis stimulation (e.g., erythropoietin); antiulcer/antireflux agents (e.g., famotidine, cimetidine, and ranitidine hydrochloride); antinauseants/antiemetics (e.g., meclizine hydrochloride, nabilone, prochlorperazine, dimenhydrinate, promethazine hydrochloride, thiethylperazine, and scopolamine); as well as other drugs useful in the compositions and methods described herein include mitotane, halonitrosoureas, anthrocyclines, ellipticine, ceftriaxone, ketoconazole, ceftazidime, oxaprozin, valacyclovir, urofollitropin, famciclovir, flutamide, enalapril, itraconazole, buspirone, gabapentin, fosinopril, tramadol, acarbose, lorazepam, follitropin, omeprazole, fluoxetine, lisinopril, tramadol, levofloxacin, zafirlukast, interferon, growth hormone, interleukin, erythropoietin, granulocyte stimulating factor, nizatidine, bupropion, perindopril, erbumine, adenosine, alendronate, alprostadil, benazepril, betaxolol, bleomycin sulfate, dexfenfluramine, diltiazem, fentanyl, flecamide, gemcitabine, glatiramer acetate, granisetron, lamivudine, mangafodipir trisodium, mesalamine, metoprolol fumarate, metronidazole, miglitol, moexipril, monteleukast, octreotide acetate, olopatadine, paricalcitol, somatropin, sumatriptan succinate, tacrine, verapamil, nabumetone, trovafloxacin, dolasetron, zidovudine, finasteride, tobramycin, isradipine, tolcapone, enoxaparin, fluconazole, lansoprazole, terbinafine, pamidronate, didanosine, diclofenac, cisapride, venlafaxine, troglitazone, fluvastatin, losartan, imiglucerase, donepezil, olanzapine, valsartan, fexofenadine, calcitonin, and ipratropium bromide. In some embodiments, the drug may be water soluble. In some embodiments, the drug may not be water soluble.

In some embodiments, the therapeutic agent may be an anti-neoplastic agent. The tei in anti-neoplastic agent may refer to any cytotoxic, or chemotherapeutic, or anti-proliferative agent. Generally speaking, the anti-neoplastic agents can vary widely depending upon the pharmacological strategy selected for slowing the growth, or actually reducing the size, of the solid tumor. The anti-neoplastic agent may be described as a single entity or a combination of entities. The compositions may include anti-neoplastic agents having high water-solubility, as well as those having low water-solubility, to produce a delivery system that has controlled release rates.

The term anti-neoplastic agent includes, without limitation, platinum-based agents, such as carboplatin and cisplatin; nitrogen mustard alkylating agents; nitrosourea alkylating agents, such as carmustine (BCNU) and other alkylating agents; anti-metabolites, such as methotrexate; purine analog antimetabolites; pyrimidine analog anti-metabolites, such as fluorouracil (5-FU) and gemcitabine; hormonal anti-neoplastics, such as goserelin, leuprolide, and tamoxifen; natural anti-neoplastics, such as taxanes (e.g., docetaxel and paclitaxel), aldesleukin, interleukin-2, etoposide (VP-16), interferon alfa, and tretinoin (ATRA); antibiotic natural anti-neoplastics, such as bleomycin, dactinomycin, daunorubicin, doxorubicin, and mitomycin; and vinca alkaloid natural anti-neoplastics, such as vinblastine and vincristine. In embodiments, the anti-neoplastic agent may be fluorouracil.

Further, the following additional drugs may also be used in combination with the anti-neoplastic agent, even if not considered anti-neoplastic agents themselves: dactinomycin; daunorubicin HCl; docetaxel; doxorubicin HCl; epoetin alfa; etoposide (VP-16); ganciclovir sodium; epinephrine; collagen; gentamicin sulfate; interferon alfa; leuprolide acetate; meperidine HCl; methadone HCl; ranitidine HCl; vinblastin sulfate; neupogen; epogen; and zidovudine (AZT). For example, fluorouracil may be combined with a vasoconstrictor to slow down the blood flow inside the tumor thereby allowing more time for tissue-stabilizing agent to cross-link the tumor.

Various forms of the anti-neoplastic agents and/or other therapeutic agents may be used. These include, without limitation, such forms as uncharged molecules, molecular complexes, salts, ethers, esters, amides, and the like, which are biologically activated when implanted, injected or otherwise inserted into the tumor.

In some embodiments, the compositions described herein may include a therapeutic agent which does not include primary amines, e.g., fluorouracil, combined with a highly amine-reactive tissue-stabilizing agent, e.g., genipin. In such embodiments, the tissue-stabilizing agent may not react with the therapeutic agent prior to administration into the tumor tissue thereby maximizing the tissue-stabilizing agent's ability to cross-link with the amine-molecules of the tumoral tissue. The more reactive the tissue-stabilizing agent, the faster the tumoral tissue will be cross-linked and the more concentrated the therapeutic agent will be within the tumor.

In other embodiments, the compositions described herein may include a therapeutic agent which includes at least one primary amine, e.g., mitomycin, combined with a highly amine-reactive tissue-stabilizing agent, e.g., genipin. In such embodiments, the compositions may further include an optional ingredient suitable for controlling the interaction between the tissue-stabilizing agent and the therapeutic agent to prevent or moderate the amount of interaction prior to administration. Some examples of useful optional ingredients include, but are not meant to be limited to, pH-modifiers, emulsifiers, lyposomes, microspheres, beads, viscosity enhancers, humectants, and the like. In this manner, the tissue-stabilizing agent may be prevented from cross-linking with the therapeutic agent thereby maintaining its ability to cross-link with the tumoral tissue upon administration. In some embodiments, the more reactive the tissue-stabilizing agent upon administration, the faster the tumoral tissue will be cross-linked and the more concentrated the therapeutic agent will be within the tumor. In other embodiments, the more reactive the tissue stabilizing agent upon administration, the slower the elution of the therapeutic agent from the tumor into the surrounding tissue.

The therapeutic agents may be used in amounts that are therapeutically effective, which varies widely depending largely on the particular therapeutic agent being used. The amount of therapeutic agent incorporated into the composition also depends upon the desired release profile, the concentration of the agent required for a biological effect, and the length of time that the therapeutic agent should be released for treatment. For example, since the injections may be intratumorally administered, the dose of the therapeutic agent may be higher or lower than what would be administered systemically.

There is no critical upper limit on the amount of therapeutic agent incorporated except for that of an acceptable solution or dispersion viscosity to maintain the physical characteristics desired for the composition. The lower limit of the therapeutic agent incorporated into the delivery system is dependent upon the activity of the drug and the length of time needed for treatment. Thus, the amount of the therapeutic agent should not be so small that it fails to produce the desired physiological effect, nor so large that the therapeutic agent is released in an uncontrollable manner.

Typically, within these limits, amounts of the therapeutic agents from about 0.1% up to about 95%, and preferably from about 1% to about 70% by weight, can be incorporated into the present compositions. However, lesser amounts may be used to achieve efficacious levels of treatment for therapeutic agents that are particularly potent.

In many cases, the compositions for intratumoral administration may be delivered as a composition comprising the tissue-stabilizing agent, the therapeutic agent and a pharmaceutically acceptable carrier in which they may be mixed or dissolved. However, other products may be added, if desired, to maximize tissue-stabilization time, drug-delivery, preservation of shelf-life, or to optimize a particular method of delivery.

A "pharmaceutically acceptable carrier" includes any and all solvents, dispersion media, coatings, isotonic and absorption delaying agents, buffering agents, and the like, compatible with intratumoral administration. Particularly useful examples of such carriers include, but are not limited to, water, saline, buffers (Hanks, Sorensen's) surfactants (tweens, pluronics, etc.), dispersing agents, Ringer's Lactate solutions and dextrose solution. For intratumoral injection, phosphate buffered saline may be a suitable carrier for the compositions described herein. It is envisioned that the volume of the pharmaceutical carrier may vary according to the specific tissue-stabilizing agents and therapeutic agents selected and their respective solubilities with the carrier.

The compositions described herein may be formulated to be compatible with the intended route of administration, such as intratumoral injection or intratumoral implantation. Solutions, suspensions, dispersions, or emulsions may be used for such administrations and may include a sterile diluent, such as water for injection, saline solution, polyethylene glycols, glycerine, propylene glycol or other synthetic solvents; antibacterial agents such as benzyl alcohol or methylparabens; antioxidants such as ascorbic acid or sodium bisulfate; buffers such as acetates, citrates or phosphates, and agents for the adjustment of tonicity such as sodium chloride or dextrose. The pH may be adjusted with acids or bases, such as hydrochloric acid or sodium hydroxide. Preparations may be enclosed in ampules, disposable syringes or multiple dose vials made of glass or plastic.

Sterile compositions for intratumoral delivery may be prepared by incorporating at least one stabilizing agent and at least one therapeutic agent in the suitable amount of a carrier, followed by sterilization. Any suitable method of sterilization may be used including steam sterilization, sterile filtration, chemical sterilization, such as exposure to ethylene oxide, and radiation sterilization, such as gamma radiation, electron beam processing, and ultraviolet light irradiation.

The compositions can be included in a kit, container, pack or dispenser, together with medical devices suitable for delivering the compositions intratumorally. The compositions included in kits may be supplied in containers of any sort such that the life of the different components may be preserved and may not be adsorbed or altered by the materials of the container. For example, sealed glass ampules or vials may contain the compositions described herein that have been packaged under a neutral non-reacting gas, such as nitrogen. Ampules may consist of any suitable material, such as glass, organic polymers, such as polycarbonate, polystyrene, etc., ceramic, metal or any other material typically employed to hold reagents. Other examples of suitable containers include bottles that are fabricated from similar substances as ampules, and envelopes that consist of foil-lined interiors, such as aluminum or an alloy. Other containers include test tubes, vials, flasks, bottles, syringes, etc. Some containers may have a sterile resealable access port, such as a bottle having a stopper that may be pierced repeatedly by a hypodermic injection needle.

The therapeutic composition may be administered by a variety of routes. For example, it may be injected directly into the solid tumor being treated with a needle, such as a Turner Biopsy Needle or a Chiba Biopsy Needle. When treating a solid tumor in the lung, for example, the composition may be administered within the thorax using a bronchoscope or other device capable of cannulating the bronchial. Masses accessible via the bronchial tree may be directly injected by using one of the widely available transbronchial aspiration needles.

The composition may also be implanted within the solid tumor using any suitable method known to those skilled in the art of penetrating tumor tissue. Such techniques may include creating an opening into the tumor and positioning the composition in the tumor.

The compositions of the present disclosure may be used to treat a solid tumor in a mammal by combining a tissue-stabilizing agent with a therapeutic agent in a pharmaceutically acceptable carrier to form the composition and administering the composition intratumorally.

As shown in FIG. 1A, needled syringe 10 contains composition 40 which includes at least one tissue-stabilizing agent, at least one therapeutic agent, and a pharmaceutically acceptable carrier. Needled syringe 10 passes through skin 30 of a mammalian subject and penetrates tumor 20 delivering composition 40 to the inside of tumor 20. It is envisioned that the composition may be delivered to different portions of the tumor by movement of the needle to other segments of the tumor. It is further envisioned that the composition may be delivered to different portions of the tumor by simple diffusion.

Figure 1B:
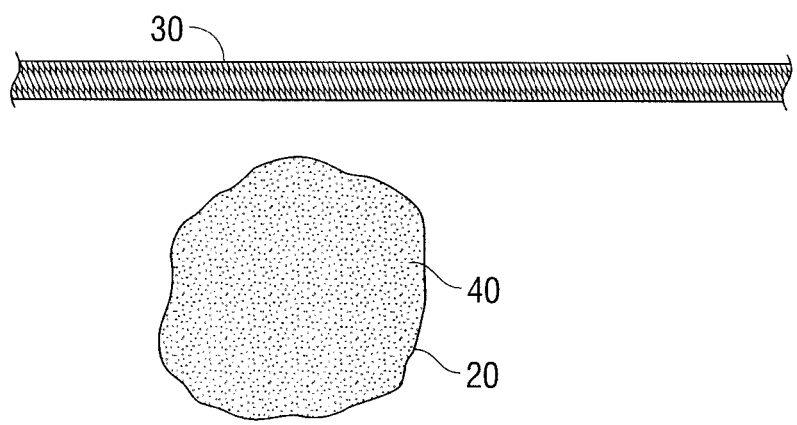

As depicted in FIG. 1B, following the delivery of composition 40 intratumorally to tumor 20, the needle may be withdrawn from the mammalian subject and composition 40 may begin to cross-link with the tumoral tissue thereby substantially inhibiting the migration of the therapeutic agent from the site of administration Inhibiting the migration of the therapeutic agent may prolong and enhance the therapeutic effect of the agent against the tumoral tissue. Tissue stabilization via cross-linking may also improve tissue stiffness and further slow tumor proliferation and/or metastasis.

Example

Genipin and fluorouracil are mixed in a phosphate buffered saline to form a solution. The concentration of the genipin in the solution is 20 mg/ml. The concentration of the fluorouracil in the solution is 50 mg/ml. The mixture is manufactured under sterile conditions in a syringe equipped with a needle.

In use, the sterile packaging is removed and the genipin and fluorouracil solution is administered intratumorally into a primary breast lesion. Over the next 4 to 8 hours, the genipin reacts with a primary amine functionality of the tumor tissue, cross-linking and coloring the tumor tissue brilliant blue. The fluorouracil is diffused through the crosslinked tumor, and retained locally and directly therein, and some portion of the drug drains to the local lymphatics, serving as a controlled release reservoir.

It will be understood that various modifications may be made to the embodiments disclosed herein. For example, the compositions may include more than one tissue-stabilizing agent. As another example, the compositions may include more than one therapeutic agent and/or carriers. Thus, those skilled in the art will envision other modifications within the scope and spirit of the claims.

What is claimed is:

1. A method for localizing a therapeutic agent, wherein the therapeutic agent is fluorouracil, inside a tumor comprising: combining genipin with fluorouracil in a pharmaceutically acceptable carrier to form a composition, and administering the composition intratumorally, wherein the genipin cross-links in-situ with tumoral tissue to create a hardened mass of tumoral tissue which inhibits the migration of the fluorouracil to prolong a local effect of the fluorouracil inside the tumoral tissue.

2. The method of claim 1 wherein the pharmaceutically acceptable carrier comprises a carrier selected from the group consisting of water, saline, Ringer's Lactate solutions and dextrose solution.

3. The method of claim 1 wherein the pharmaceutically acceptable carrier comprises phosphate buffered saline.

4. The method of claim 1 wherein the composition further comprises a pH-modifier.

5. The method of claim 1 wherein the step of administering the composition intratumorally comprises injecting the composition into a tumor.

6. The method of claim 1 wherein the step of administering the composition intratumorally comprises implanting the composition into a tumor.

7. The method of claim 1 wherein the genipin represents from about 1 to about 70% by weight of the composition.

8. The method of claim 1 wherein the therapeutic agent represents from about 1 to about 70% by weight of the composition.

\* \* \* \* \*